(12) United States Patent
Baltzell

(10) Patent No.: US 7,670,629 B2
(45) Date of Patent: Mar. 2, 2010

(54) METHOD OF TREATING BACTERIAL HOOF INFECTIONS OF SHEEP AND CATTLE

(76) Inventor: Robert Baltzell, 6930 F. St., Omaha, NE (US) 68117

( * ) Notice: Subject to any disclaimer, the term of this patent is extended or adjusted under 35 U.S.C. 154(b) by 47 days.

(21) Appl. No.: 11/314,561

(22) Filed: Dec. 21, 2005

(65) Prior Publication Data

US 2007/0141172 A1 Jun. 21, 2007

(51) Int. Cl.
*A61K 33/30* (2006.01)
*A01N 25/00* (2006.01)

(52) U.S. Cl. .......................... 424/642; 424/405

(58) Field of Classification Search .................. 424/642
See application file for complete search history.

(56) References Cited

U.S. PATENT DOCUMENTS

| | | | |
|---|---|---|---|
| 2,299,604 A | 10/1942 | Welrich | 167/30 |
| 4,008,332 A | 2/1977 | Thomas | 424/334 |
| 4,164,477 A | 8/1979 | Whitley | 252/99 |
| 4,268,504 A * | 5/1981 | Harrington et al. | 424/637 |
| 4,299,613 A * | 11/1981 | Cardarelli | 71/64.11 |
| RE33,512 E | 1/1991 | Ramirez et al. | 424/641 |
| 5,648,389 A | 7/1997 | Gans et al. | 514/557 |
| 5,780,064 A * | 7/1998 | Meisters et al. | 424/616 |
| 6,093,422 A | 7/2000 | Denkewicz, Jr. et al. | 424/618 |
| 6,183,785 B1 | 2/2001 | Westfall | 424/642 |
| 6,294,186 B1 | 9/2001 | Beerse et al. | 424/405 |
| 6,344,218 B1 * | 2/2002 | Dodd et al. | 424/605 |
| 6,617,296 B1 | 9/2003 | Connors et al. | 510/221 |
| 2004/0176312 A1 * | 9/2004 | Gillis | 514/36 |

FOREIGN PATENT DOCUMENTS

GB 2 141 929 A * 1/1985

OTHER PUBLICATIONS

Hauptmeier, Larry D. 'Footrot in Beef Cattle' [online] Iowa Beef Center, Mar. 1997, Retrieved from the Internet: <URL: http://www.iowabeefcenter.org/Publications/footrot.pdf> on Jul. 9, 2007.*
Nigel B. Cook, "Footbath alternatives", provided by DeLaval online at http://www.milkproduction.com/Library/Articles/Footbath_Alternatives.htm, published Mar. 28, 2007.*
Abbott, KA; Lewis, CJ, *Current approaches to the management of ovine footrot*, Abstract: Vet J. Jan. 2005;169(1) : 28-41.
Cook, NB, *Foot Bath Operation for the Control of Infectious Diseases of the Hoof in Dairy Cattle*, University of Wisconsin-Madison, Nov. 2004.
Davis, J and Wailes, B, *Is Copper in Dairy Footbaths a Problem for Crops and Cows?*, Agronomy News, Nov.-Dec. 2001, vol. 21:Issue 6.
Gradin, JL; Schmitz, JA, *Susceptibility of Bacteroides nodosus to various antimicrobial agents*, Abstract: J Am Vet Med Assoc. Aug. 15, 1983; 183(4) : 434-7.
Jelinek, PD; Depiazzi LJ; Galvin, DA; Spicer, IT, Palmer, MA; Pitman, DR, *Eradication of ovine footrot by repeated daily footbathing in a solution of zinc sulphate with surfactant*, Aust Vet J. Jun. 2001;79(6) : 431-4.

Jelinek, PD; Depiazzi, LJ, *Failure to eradicate ovine footrot associated with Dichelobacter nodosus strain A198 by repeated daily footbathing in zinc sulphate with surfactant.*, Aust Vet J. Jan.-Feb. 2003;81 (1-2) : 58-62.
Kimberling, CV; Ellis, RP, *Advances in the control of foot rot in sheep*, Abstract: Vet Clin North Am Food Anim Pract. Nov. 1990; 6(3) : 671-81.
Laven, RA; Hunt, H, *Evaluation of copper sulphate, formalin and peracetic acid in footbaths for the treatment of digital dermatitis in cattle*, Abstract: Vet Rec. Aug. 3, 2002;151(5) : 144-6.
Maas, J, *Footrot*, California Cattleman, Jun. 1995.
Malecki, JC; McCausland, IP, *In vitro penetration and absorption of chemicals into the ovine hoof*, Abstract: Res Vet Sci. Sep. 1982;33 (2) : 192-7.
Malecki, JC; Coffey, L, *Treatment of ovine virulent footrot with zinc sulphate/sodium lauryl sulphate footbathing*, Abstract: Aust Vet J. Oct. 1987;64(10) : 301-4.
Ortolani, EL; Antonelli, AC, de Souza Sarkis, JE, *Acute sheep poisoning from a copper sulfate footbath*, Abstract: Vet Hum Toxicol. Dec. 2004;46(6) : 315-8.
Parajuli, B; Goddard, PJ, *A comparison of the efficacy of footbaths containing formalin or zinc sulphate in treating ovine foot-rot under field conditions*, Abstract: Br Vet J. Sep.-Oct. 1989;145(5) : 467-72.
Reed, GA; Alley, DU, *Efficacy of a novel copper-based footbath preparation for the treatment of ovine footrot during the spread period*, Abstract: Aust Vet J. Nov. 1996;74(5) : 35-82.
Shearer, JK; van Amstel, SR, *Managing Lameness for Imporved Cow Comfort and Performance*, Proceedings of the 6th Western Dairy Management Conference; Mar. 12-14, 2003; Reno, NV : 167-177.
Skerman, TM; Green, RS; Hughes, JM; Herceg, M, *Comparison of footbathing treatments for ovine footrot using formalin or zinc sulphate*, Abstract: N Z Vet J. Jun. 1983;31(6) : 91-5.
Skerman, TM; Moorhouse, SR; Green RS, *Further investigations of zinc sulphate footbathing for the prevention and treatment of ovine footrot*, Abstract: N A Vet J. Jun. 1983;31(6) : 100-2.
Skerman, TM; Moorhouse, SR; Green, RS, *Further investigations of zinc sulphate footbathing for the prevention and treatment of ovine footrot*, Abstract: N Z Vet J. Sep. 1983;31(9) : 151.
Whittier, WD; Umberger, SH, *Control, Treatment, and Elimination of Foot Rot from Sheep*, Virginia Cooperative Extension; Sheep; Publication 410-028, Reprinted 1997.

* cited by examiner

*Primary Examiner*—Johann R Richter
*Assistant Examiner*—Nathan W Schlientz
(74) *Attorney, Agent, or Firm*—Wood, Herron & Evans, L.L.P.

(57) ABSTRACT

Bacterial infections in cattle and sheep are treated by applying a solution of zinc chloride to the hooves of the animals. Preferably, the solution is applied to the hooves by placing the solution in a foot bath and guiding the animals through the foot bath. The spent solution can then be mixed with manure and applied to the fields. The zinc acts as a micronutrient.

6 Claims, No Drawings

METHOD OF TREATING BACTERIAL HOOF INFECTIONS OF SHEEP AND CATTLE

BACKGROUND OF THE INVENTION

Sheep and cattle are prone to bacterial hoof infections that can be quite debilitating. A common condition in cattle is "foot rot" or what is medically termed interdigital phlegmon. It is an infection of the soft tissue between the claws of the feet and is caused by two anaerobic bacteria, *Fusobacterium necrophorum* and *Prevotella melaninogenicus* (formerly known as *Bacteroides melaninogenicus*). These bacteria are common in the environment and *F. necrophorum* is present in the rumen and feces of normal cattle. Once these bacteria invade the skin of the foot, they rapidly cause the condition we recognize as foot rot. Injury or damage to the skin between the claws allows this invasion to occur. Common factors that can cause damage of this sort include stubble fields, small rocks and pebbles, and abrasive surfaces. Additionally, high temperatures and excess moisture or humidity causes the skin between the claws to chap and crack allowing these bacteria to invade.

Ovine foot rot is caused by an interaction of two anaerobic, Gram (−) bacteria, *Dichelobacter nodosus* (formerly known as *Bacteroides nodosus* and *Fusiformis nodosus*) and *Fusobacterium necrophorum*. *Fusobacterium necrophorum* is a normal inhabitant of the ruminant digestive tract and in wet weather may interact with another bacteria, *Corynebacterium pyogenes,* to produce foot scald, an infection of the skin between the toes. This infection sets up the foot for invasion by *D. nodosus,* which produces the condition referred to as foot rot.

Farmers typically take steps to avoid foot rot. One common practice is to utilize a foot bath for the sheep or cows. This is not only an effective preventive measure, it is an effective treatment for such bacterial infections.

There are two different types of solutions commonly used in foot baths: zinc sulfate and copper sulfate. For treatment, they should be used 1-2 times per week for several weeks. They may also be used routinely after foot trimming and as a preventative. Predominantly, copper sulfate is the solution of choice for treating foot rot, particularly with cattle. Zinc sulfate, although somewhat effective, has shown mixed results.

The use of copper sulfate presents environmental concerns. The foot bath solution is typically drained into the manure store and is subsequently applied to the fields. Excess copper can be hazardous to the cattle and sheep. The application of the copper-laden manure onto the fields causes a copper build-up, which can be problematic to the plants' development and, therefore, should be avoided.

Zinc sulfate does not have this problem. However, as indicated, it is not as well accepted nor considered to be as effective as copper sulfate. Further, zinc sulfate and copper sulfate are acidic in solution. A more acidic treatment reduces the desired contact time. This reduces efficacy. Other treatments, such as the use of formalin have other disadvantages.

SUMMARY OF THE INVENTION

The present invention is premised on the realization that bacterial hoof infections of cows and sheep can be treated with an aqueous solution of zinc chloride. More particularly, the present invention involves the application of a solution of zinc chloride, typically using a foot bath, to effectively treat and prevent foot rot and other bacterial infections of sheep and cattle. The objects and advantages of the present invention will be further appreciated in light of the following detailed description.

DETAILED DESCRIPTION OF THE INVENTION

Bacterial infections of sheep and cattle are treated with an aqueous solution of zinc chloride. Zinc chloride can come from a variety of different sources and can be obtained as an aqueous solution or a solid which is dissolved in water to achieve an effective concentration.

The effective concentration of the zinc chloride solution is preferably 2% to about 20% by weight, with about 5% by weight preferred for prevention and 10% by weight for curing existing infections.

The preferred method to apply the solution of zinc chloride to the hooves of sheep or cattle is the use of a walk through foot bath. More particularly, the animals are simply directed through the foot bath. Preferably, the foot baths will be about 6 inches deep of the zinc chloride so the solution should be filled to a depth of at least 4 inches, slightly less for sheep. The foot bath should be 8 to 12 feet long and is preferably preceded by a wash bath containing only water, or water and detergent, to remove manure from the feet prior to passing through the treatment bath. The treatment bath will typically be drained to the manure store.

Preferably, the chemical in the treatment bath is changed after about 200 animals have passed through the bath. The bath should then be thoroughly rinsed and cleaned prior to subsequent use.

The manure store with the drained zinc chloride solution can then be processed in the normal operation and subsequently deposited onto the fields. The zinc acts as a nutrient for the plants and has no adverse environmental impact. The efficacy of the present invention is demonstrated by the following example.

EXAMPLE

Tests were conducted to determine the antibacterial activity of zinc chloride relative to zinc sulfate and copper sulfate against two bacteria typically associated with foot rot in cattle. The bacterial strains used for this study were obtained from the American Type Culture Collection (ATCC).

Bacterial Preparations

*Prevotella melaninogenica* ATCC No. 25845

*Fusobacterium necrophorum* ATCC No. 25286

Dehydrated bacteria were resuspended in 5 mL of Brain Heart Infusion (BHI) broth and incubated anaerobically for 48 hours at 37° C. A total of 20 uL of each resuspended bacterial solution was plated on two 5% Trypticase Sheep Blood Agar (BA) plates and incubated anaerobically for 48 hours at 37° C. to ensure that a pure culture was maintained throughout the resuspension process. Six (6) vials of each bacterium were frozen down from the resuspended broth in a 20% glycerol solution (500 uL bacteria: 500 uL 40% glycerol).

One vial from the frozen stock of each bacterial strain was grown in 100 mL of Difco Anaerobe Broth MIC. *P. melaninogenica* was grown anaerobically for 24 hours at 37° C. and *F. necrophorum* was grown anaerobically for 48 hours at 37° C. After incubation, one hundred (100) 1 mL-vials of each bacterium were frozen down in a 10% glycerol solution.

Colony forming units/mL (CFU/mL) for each bacterium was determined by thawing 3 vials of each bacteria and making serial 1:10 dilutions out to $10e^{-7}$. Separate serial dilutions were made for each of the three vials. A total of 100 uL of dilutions $10e^{-3}$, $10e^{-4}$, $10e^{-5}$, $10e^{-6}$, and $10e^{-7}$ were plated in duplicate for each vial on BA plates and incubated under the appropriate culture conditions for each. The number of colonies growing on each dilution plate was counted and the CFU/mL for each dilution was determined. The average CFU/mL for each bacterium was calculated and used for all further assays.

| Bacteria | CFU/mL |
|---|---|
| *P. melaninogenica* | 2.38e7 |
| *F. necrophorum* | 9.75e5 |

Bacterial Inhibition Assay

The ZnCl arrived as a 60% solution and was diluted with distilled water to achieve concentrations of 2.5%, 5%, 10%, and 15% by weight. The $ZnSO_4$ and $CuSO_4$ arrived as dehydrated powder and were resuspended in distilled water to achieve 2.5%, 5%, 10%, and 15% solutions. All mineral concentrations were filter-sterilized to ensure sterility.

To determine whether different concentrations of mineral salt solutions can inhibit the growth of an established culture, a separate blank paper disc was infused with each concentration of mineral salt solution and placed onto BA plates that had been swabbed with established cultures of each bacterium. Plates were incubated anaerobically for 48 hours and the zone (in mm) around each disc with no bacterial growth was measured with a caliper. The assay was repeated three times, and the mean zone of inhibition for each mineral concentration was calculated.

pH Measurement

The pH of all the mineral salt concentrations was determined (Table 1). The pH of the $ZnCl_2$ was less acidic than that of both the $ZnSO_4$ and $CuSo_4$ at all of the concentrations.

TABLE 1 pH measurements of mineral salt solutions

| | Concentration | | | |
|---|---|---|---|---|
| Mineral | 2.5% | 5% | 10% | 15% |
| $ZnSO_4$ | 5.06 | 4.75 | 4.34 | 4.16 |
| $ZnCl_2$ | 6.02 | 5.78 | 5.43 | 5.21 |
| $CuSO_4$ | 4.34 | 4.13 | 3.94 | 3.81 |

Statistical Analysis

Data were analyzed using the Mixed Model procedure of SAS (PROC MIXED; SAS Stat Inc., Cary, N.C.) to test the effect of different concentrations for each mineral on *P. melaninogenica* and *F. necrophorum*. Least square means were calculated and separated using the PDIFF option of SAS. Contrast statements of SAS were used to determine linear and quadratic effects. The plate was used as the experimental unit. An alpha level of 0.05 was used to assess the significance in this experiment.

Results and Discussion

The zone of inhibition of *P. melaninogenica* linearly increased as the concentration of the three minerals increased (P<0.001, Table 2). At each of the concentrations, there was a significantly greater zone of inhibition for $ZnCl_2$ compared to the other two minerals (P=0.01). The zone of inhibition was not significantly different between $CuSO_4$ and $ZnSO_4$ at each of the concentrations.

The zone of inhibition of *F. necrophorum* linearly increased as the concentration of the three minerals increased (P<0.001; Table 3). At each of the concentrations, the zone of inhibition was the greatest for $CuSO_4$ and smallest for $ZnSO_4$, and the zone of inhibition of $ZnCl_2$ fell intermediate to the other two minerals at all the concentrations (P<0.01).

TABLE 2

Effect of different levels of mineral solution on zone of inhibition of *Prevotella melaninogenica*

| | Concentration | | | | | P value | |
|---|---|---|---|---|---|---|---|
| Mineral | 2.5% | 5% | 10% | 15% | SEM[1] | Linear | Quadratic |
| $ZnCl_2$ | 38.9[b] | 42.5[b] | 46.6[b] | 52.0[b] | 1.15 | 0.0001 | 0.003 |
| $ZnSO_4$ | 29.3[a] | 33.5[a] | 38.6[a] | 42.9[a] | 0.66 | 0.0001 | 0.001 |
| $CuSO_4$ | 31.0[a] | 31.7[a] | 38.2[a] | 40.7[a] | 1.53 | 0.0001 | 0.04 |
| SEM[1] | 1.07 | 1.23 | 1.08 | 1.24 | | | |

[1]Standard error of the least square means.
[a,b,c]Values with different letters in the same column differ (P < 0.01).

TABLE 3

Effect of different levels of mineral solution on zone of inhibition of *Fusobacterium necrophorum*

| | Concentration | | | | | P value | |
|---|---|---|---|---|---|---|---|
| Mineral | 2.5% | 5% | 10% | 15% | SEM[1] | Linear | Quadratic |
| $ZnCl_2$ | 27.6[b] | 33.9[b] | 41.3[b] | 44.2[b] | 0.93 | 0.0001 | 0.006 |
| $ZnSO_4$ | 25.0[a] | 29.5[a] | 35.8[a] | 40.4[a] | 0.69 | 0.0001 | 0.001 |
| $CuSO_4$ | 36.3[c] | 40.7[c] | 46.7[c] | 52.2[c] | 1.13 | 0.0001 | 0.002 |
| SEM[1] | 0.29 | 1.18 | 0.74 | 1.00 | | | |

[1]Standard error of the least square means.
[a,b,c]Values with different letters in the same column differ (P < 0.01).

SUMMARY

Overall, the $ZnCl_2$ and $CUSO_4$ mineral solutions had the greatest antibacterial effect on both *P. melaninogenica* and *F. necrophorum;* however, the $ZnSO_4$ mineral solutions had only slightly less antibacterial activity. The pH's of the $ZnSO_4$ and $CuSO_4$ were more acidic than the pH of the $ZnCl_2$ at all concentrations.

Thus, as shown above, zinc chloride is more effective than zinc sulfate and as effective as copper sulfate, but is less acidic, thus allowing the animals to spend additional time in the bath without adversely affecting the hoof. Further, the zinc chloride has a beneficial environmental impact as opposed to the negative impact of the copper sulfate.

This has been a description of the present invention along with the preferred method of practicing the invention. However, the invention itself should be defined by the appended claims, Wherein I claim:

1. A method of treating hooves of cattle to reduce bacterial infections in said hooves comprising:
    applying a treatment solution consisting of an aqueous solution of zinc chloride onto said hooves of said cattle.
2. The method claimed in claim 1 wherein said treatment solution contains about 3% to about 20% zinc chloride by weight.
3. The method claimed in claim 2 wherein said treatment solution is placed in a foot bath and said animals are directed through said foot bath.

4. The method claimed in claim 3 wherein said solution in said foot bath is subsequently applied to fields.

5. The method claimed in claim 1 wherein said solution has a pH of greater than about 4.5.

6. A method of treating hooves of animals to reduce bacterial infections in said hooves comprising applying to said hooves a treatment solution consisting of zinc chloride and water onto said hooves of said animals.

* * * * *